US009448394B2

(12) United States Patent
Mandella et al.

(10) Patent No.: US 9,448,394 B2
(45) Date of Patent: Sep. 20, 2016

(54) ARRAYED DUAL AXIS CONFOCAL MICROSCOPES

(71) Applicant: The Board of Trustees of the Leland Stanford Junior University, Palo Alto, CA (US)

(72) Inventors: Michael J. Mandella, Palo Alto, CA (US); Olav Solgaard, Stanford, CA (US); Christopher H. Contag, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/209,839

(22) Filed: Mar. 13, 2014

(65) Prior Publication Data

US 2014/0268318 A1 Sep. 18, 2014

Related U.S. Application Data

(60) Provisional application No. 61/782,384, filed on Mar. 14, 2013.

(51) Int. Cl.
*G02B 21/00* (2006.01)
*A61B 5/00* (2006.01)

(52) U.S. Cl.
CPC ......... *G02B 21/0048* (2013.01); *A61B 5/0068* (2013.01); *G02B 21/008* (2013.01); *A61B 5/0071* (2013.01)

(58) Field of Classification Search
CPC ............ G02B 21/002; G02B 21/0024; G02B 21/0036; G02B 21/0048; G02B 21/008; G02B 21/18; G02B 21/36; G02B 21/361; G02B 17/00; G02B 17/02; G02B 17/023; G02B 17/06; G02B 17/0605; G02B 17/0615; G02B 17/0621; G02B 17/0626; G02B 17/0636; G02B 17/0642; G02B 17/0647; G02B 17/0657; G02B 17/0663; G02B 26/0816; G02B 26/10; G02B 26/101; G02B 26/105; G02B 26/0833–26/0866; G02B 3/0087; A61B 5/0068; A61B 5/0071; A61B 5/0062; A61B 5/0059; A61B 5/0084; A61B 5/1459; A61B 1/00163; A61B 1/00165; A61B 1/00172; A61B 1/04; A61B 1/041; A61B 1/043; A61B 1/06; A61B 1/0661–1/0684; A61B 1/07
See application file for complete search history.

(56) References Cited

U.S. PATENT DOCUMENTS 4,275,962 A * 6/1981 Midorikawa et al. ............ 355/1
5,742,419 A 4/1998 Dickensheets et al.
(Continued)

OTHER PUBLICATIONS

Leigh, S.Y. and Liu, J.T.C. "Multi-color miniature dual-axis confocal microscope for point-of-care pathology." Optics Letters 37(12), pp. 2430-2432 (Jun. 15, 2012).
(Continued)

*Primary Examiner* — Stephone B Allen
*Assistant Examiner* — Adam W Booher
(74) *Attorney, Agent, or Firm* — Crawford Maunu PLLC

(57) ABSTRACT

Various aspects as described herein are directed to apparatuses, methods, and systems including a sandwiched arrangement having a light-access port, a scanning mirror, an optics region, and a spacer. The spacer provides a light-directing optical region that separates the scanning mirror and the optics region, and includes a mirrored surface that reflects light between the light-access port and the optics region. Additionally, the optics region includes a curved-shaped window that provides a field of view by communicating beams of light between a target region. The optics region also includes a curved-shaped mirror having a surface that reflects light between the scanning mirror and the mirrored surface. Light beams, as conveyed between the light-access port and the curved-shaped window, are folded by being reflected off the scanning mirror, the curved-shaped mirror and the mirrored surface.

17 Claims, 13 Drawing Sheets

(56) References Cited

U.S. PATENT DOCUMENTS

| | | |
|---|---|---|
| 6,411,835 B1 * | 6/2002 | Modell et al. ............... 600/407 |
| 6,414,779 B1 | 7/2002 | Mandella et al. |
| 6,710,316 B2 | 3/2004 | Mandella et al. |
| 6,713,742 B2 | 3/2004 | Mandella et al. |
| 7,095,505 B1 | 8/2006 | Beard et al. |
| 7,242,521 B2 | 7/2007 | Mandella et al. |
| 7,448,995 B2 | 11/2008 | Wiklof et al. |
| 7,843,620 B2 | 11/2010 | Pinter |
| 8,273,015 B2 | 9/2012 | Youmans et al. |
| 8,332,014 B2 | 12/2012 | Youmans |
| 2002/0141714 A1 * | 10/2002 | Reed et al. ................ 385/116 |
| 2012/0330157 A1 | 12/2012 | Mandella et al. |

OTHER PUBLICATIONS

Levoy, M., Zhang, Z. and McDowall, I. "Recording and controlling the 4D light field in a microscope using microlens arrays." J. of Microscopy 235(2), pp. 144-162 (2009).

Piyawattanametha, W. and Wang, T.D. "Miniature Dual Axes Confocal Microscope for Real Time In Vivo Imaging." Advances in Solid State Circuits Technologies, Ch. 19, pp. 393-430 (Apr. 1, 2010).

* cited by examiner

ARRAYED DUAL AXIS CONFOCAL MICROSCOPES

FIELD

This invention relates to confocal microscopy.

OVERVIEW

Confocal microscopy is a biomedical imaging technique useful for optical sectioning of tissues to image structure and function with cellular and sub-cellular resolution. Confocal microscopy can be used in reflectance imaging to reveal anatomic features, as well as fluorescence imaging for the detection of molecular indicators of cellular function.

High-resolution imaging tools can be coupled with informative reporters that can be useful for pathology. For instance, such high-resolution imaging tools can be used as scanning cytometers assessing fluorescence intensity and counting cell numbers (such as the status of individual cells in human tumor tissues). However, confocal microscopes have traditionally been large bench top devices, which increases the spatiotemporal separation between a pathologist and a patient.

SUMMARY OF THE INVENTION

Various aspects of the present disclosure are directed toward apparatuses that include a sandwiched region. One such the sandwiched region includes a light-access port, a scanning mirror, an optics region, and a spacer. The spacer can be configured to provide a light-directing optical region that separates the scanning mirror and the optics region. Further, the spacer can also include a mirrored surface that reflects light between the light-access port and the optics region. The optics region, in certain embodiments, includes a curved-shaped window that provides a field of view by communicating beams of light between a target region, located in a direction opposite the scanning mirror, and the light-directing optical region.

The optics region can also include a curved-shaped mirror having a surface that reflects light between the scanning mirror and the mirrored surface. In such embodiments, light beams, as conveyed between the light-access port and the curved-shaped window, are folded by being reflected off the scanning mirror, the curved-shaped mirror and the mirrored surface. Additionally, the optics region, in certain embodiments, includes first means for providing a field of view by communicating beams of light between a target region, located in a direction opposite the scanning mirror, and the light-directing optical region. The optics region can also include second means for reflecting light between the scanning mirror and the mirrored surface. In these such embodiments, the light beams, as conveyed between the light-access port and the first means, are folded by being reflected off the scanning mirror, the second means and the mirrored surface.

Various aspects of the present disclosure are directed toward methods for use in a sandwiched arrangement including a light-access port, a scanning mirror and an optics region. Such methods can include using a spacer to provide a light-directing optical region that separates the scanning mirror and the optics region. The spacer includes a mirrored surface that reflects light between the light-access port and the optics region. Additionally, the methods can also include using a curved-shaped window, in the optics region, to provide a field of view by communicating beams of light between a target region, located in a direction opposite the scanning mirror, and the light-directing optical region. Further, the methods can include using a curved-shaped mirror, in the optics region, to reflect light between the scanning mirror and the mirrored surface. Moreover, the methods can also include folding light beams, as conveyed between the light-access port and the curved-shaped window, by reflecting the light beams via the scanning mirror, the curved-shaped mirror and the mirrored surface.

The above discussion/summary is not intended to describe each embodiment or every implementation of the present disclosure. The figures and detailed description that follow also exemplify various embodiments.

BRIEF DESCRIPTION OF THE FIGURES

Various example embodiments may be more completely understood in consideration of the following detailed description in connection with the accompanying drawings.

Figure 1:
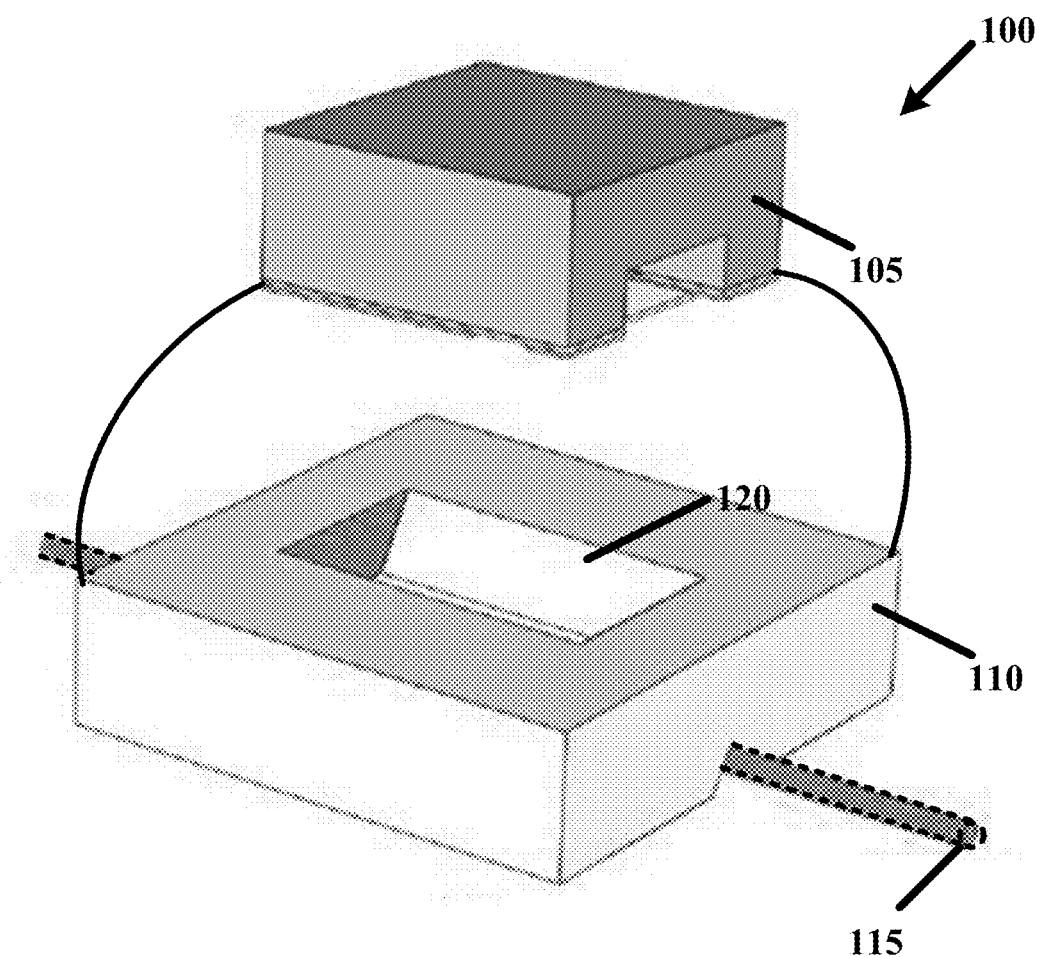
FIG. 1 shows an example sandwiched arrangement, consistent with various aspects of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DESCRIPTION OF EXAMPLE EMBODIMENTS

Various aspects of the present disclosure are directed towards apparatus, methods of use, and methods of manufacturing of sandwiched arrangements that can be operable as point-scanning dual Dual Axis Confocal (DAC). In certain embodiments, the multiple sandwiched arrangements can be arranged to form an array of DAC microscopes. The sandwiched arrangements can be diced from the wafer individually or in groups (e.g., yielding arrays of microscopes of single or multiple rows). The sandwiched arrangement (or array of multiple sandwiched arrangements) can be used to interrogate live two-dimensional (2-D) and three-dimensional (3-D) cell, tissue, and/or organ cultures. The sandwiched arrangements are versatile in that the arrangements can be implantable/wearable in vivo microscopes for use in humans or animals for biomedical diagnostics, and can also provide dynamic imaging of cellular behavior in living tissues as a non-invasive diagnostic tool. For instance, cancer tissue can be assessed through this dynamic imaging to determine malignancies from different types of cancers such as gastrointestinal cancers, skin cancers, and breast cancers. Further, the sandwiched arrangements can be used for performing dynamic serial imaging studies for extended periods, thus allowing for examination of the morphologic and molecular parameters of the living subject in vivo.

Various aspects of the present disclosure are directed toward apparatuses that include a sandwiched region. One such the sandwiched region includes a light-access port, a scanning mirror, an optics region, and a spacer. The spacer can be configured to provide a light-directing optical region that separates the scanning mirror and the optics region. Further, the spacer can also include a mirrored surface that reflects light between the light-access port and the optics region. The optics region, in certain apparatus embodiments, includes a curved-shaped window that provides a field of view by communicating beams of light between a target region, located in a direction opposite the scanning mirror, and the light-directing optical region. Additionally, the optics region can include a curved-shaped mirror having a surface that reflects light between the scanning mirror and the mirrored surface. In such embodiments, light beams, as conveyed between the light-access port and the curved-shaped window, are folded by being reflected off the scanning mirror, the curved-shaped mirror and the mirrored surface.

In certain more specific embodiments, the curved-shaped window is a hemispherical window, and the curved-shaped mirror is an ellipsoidal mirror. Additionally, another mirrored surface can be included in the spacer, which is oppositely situated from the other mirrored surface near end regions of the optics region. Moreover, certain apparatuses of the present disclosure also include another (second) light access port and another (second) mirrored surface in the spacer. In these such embodiments, the mirrored surfaces in the spacer are oppositely situated near end regions of the optics region, and each reflects light between a remotely-situated one of the light access ports and the optics region. Further, in certain embodiments having a second light access port, one of the light access ports illuminates the optical region with the beams of light, and the other light access port conveys collected beams of light from the light-directing optical region.

Certain embodiments of the present disclosure are also directed toward multiple apparatuses that include at least one additional sandwiched arrangement. The additional (other) sandwiched arrangement also includes a scanning mirror, an optics region, and a spacer, consistent various aspects of the present disclosure. Each of the sandwiched arrangements can include a plurality of light-access ports that pass collected beams of light between adjacently-situated sandwiched arrangements. Certain embodiments of the present disclosure include an X-by-Y array (each of X-by-Y is two or greater) of confocal microscopes. Each of the confocal microscopes is constructed according to a sandwiched arrangement, consistent with various aspects of the present disclosure. Further, in certain more specific embodiments, adjacently-situated sandwiched arrangements in the X-by-Y array of confocal microscopes, share a common field-of-view.

Certain embodiments of the sandwiched arrangement further include a surface of the optics region that interfaces with a tissue region. In certain embodiments, the sandwiched arrangement includes circuitry that captures images of the tissue region. Additionally, the sandwiched arrangement can include circuitry that captures images of the tissue region including a field-of-view of at least 300 µm by 300 µm. Further, the images can be captured at a resolution between 1-5 µm. In other certain embodiments, the scanning mirror is configured to scan the beams of light to depths in the tissue region.

Other embodiments of apparatuses including a sandwiched region include a tip that penetrates tissue with the curved-shaped window. Further, the curved-shaped window can be a tapered gradient-index (GRIN) lens that focuses beams of light near the tip.

Various aspects of the present disclosure are also directed toward systems, methods and apparatuses that include a sandwiched region having an-access port, a scanning mirror, an optics region, and a spacer. The spacer can provide a light-directing optical region that separates the scanning mirror and the optics region. Further, the spacer can also include a mirrored surface that reflects light between the light-access port and the optics region. The optics region, in certain embodiments, includes a curved-shaped window that provides a field of view by communicating beams of light between a target region, located in a direction opposite the scanning mirror, and the light-directing optical region. Additionally, the optics region, in certain embodiments, includes first means for providing a field of view by communicating beams of light between a target region, located in a direction opposite the scanning mirror, and the light-directing optical region. The first means can include a curved-shaped window or a hemispherical window. The optics region can also include second means for reflecting light between the scanning mirror and the mirrored surface. The second means can include a curved-shaped mirror, or an ellipsoidal mirror. In these such embodiments, the light beams, as conveyed between the light-access port and the first means, are folded by being reflected off the scanning mirror, the second means and the mirrored surface.

Various aspects of the present disclosure are directed toward methods for use in a sandwiched arrangement including a light-access port, a scanning mirror and an optics region. Such methods can include using a spacer to provide a light-directing optical region that separates the scanning mirror and the optics region. The spacer includes a mirrored surface that reflects light between the light-access port and the optics region. The methods can also include using a curved-shaped window, in the optics region, to provide a field of view by communicating beams of light between a target region, located in a direction opposite the scanning mirror, and the light-directing optical region. Further, the methods can include using a curved-shaped mirror, in the optics region, to reflect light between the scanning mirror and the mirrored surface. Moreover, the methods can also include folding light beams, as conveyed between the light-access port and the curved-shaped window, by reflecting the light beams via the scanning mirror, the curved-shaped mirror and the mirrored surface.

The embodiments and specific applications discussed herein may be implemented in connection with one or more of the above-described aspects, embodiments and implementations, as well as with those shown in the appended figures.

Turning now to the figures, FIG. 1 shows an example sandwiched arrangement 100, consistent with various aspects of the present disclosure. The sandwiched arrangement shown in FIG. 1 includes a scanning mirror arrangement 105, a spacer region 110 including a light-access port 115, and an optics region (as shown in further detail below in FIG. 2A with reference to item 225). The spacer 110 includes a mirrored surface 120 that reflects light between the light-access port 115 and the optics region. The optics region includes a curved-shaped window that provides a field of view by communicating beams of light. Additionally, the optics region includes a curved-shaped mirror having a surface that reflects light between the scanning mirror arrangement 105 and the mirrored surface 120. Curved-shaped mirror surface(s) can be on opposing sides of the window. The sandwiched arrangement 100 folds light beams, as conveyed between the light-access port 115 and the curved-shaped window, by reflecting the beams off the scanning mirror arrangement 105, the curved-shaped mirror and the mirrored surface 120.

FIGS. 2A-2H show an example operation of a sandwiched arrangement 200, consistent with various aspects of the present disclosure. In each of FIGS. 2A-2H, the sandwiched arrangement 200 includes a scanning mirror 205, a spacer region 210 that includes two mirrored surfaces 215, and an optics region 225. The spacer region 210 also includes a light-directing optical region 220 that separates the scanning mirror 205 and the optics region 225. In the embodiment shown, the optics region 225 is a fused silica optics plate. The optics region 225 includes a curve-shaped window 230, and curved-shaped mirrors 235. In the embodiment shown, the curve-shaped window 230 is a hemispherical window, and the curved-shaped mirrors 235 are ellipsoidal mirrors. The spacer region 210 also includes two optical fibers: an illumination fiber 240 and a collection fiber 245. In each of the below figures, a light beam 250 is shown at different points in the sandwiched arrangement 200.

Figure 2A:
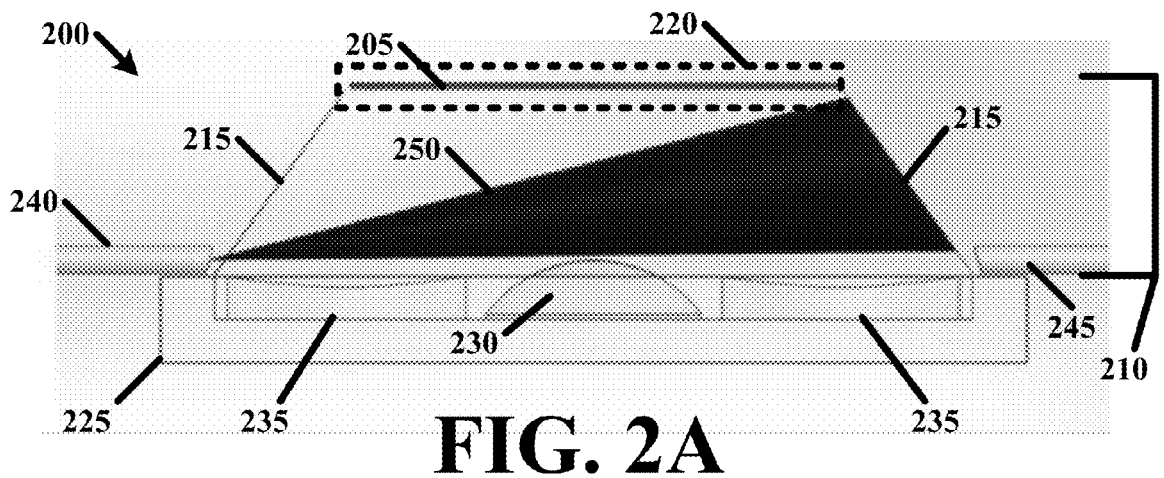
FIGS. 2A-2H show an example operation of a sandwiched arrangement, consistent with various aspects of the present disclosure.
Figure 2B:
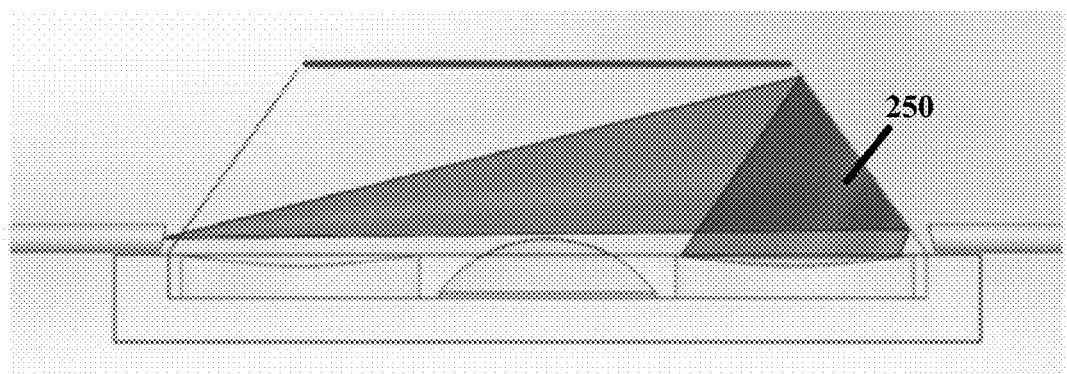
Figure 2C:
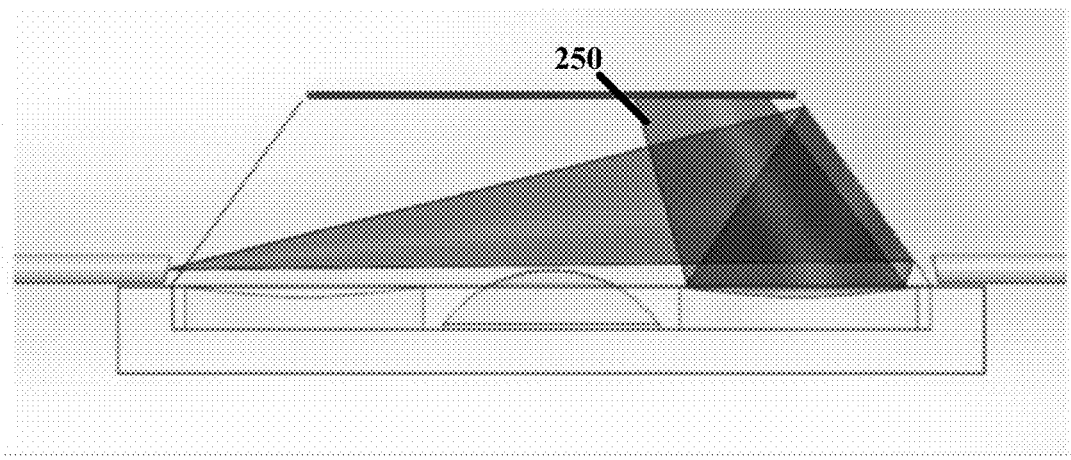
Figure 2D:
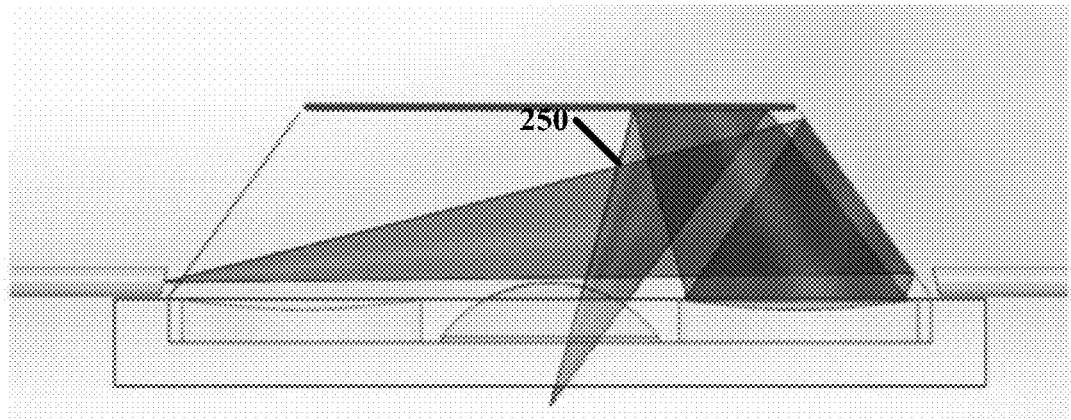
Figure 2E:
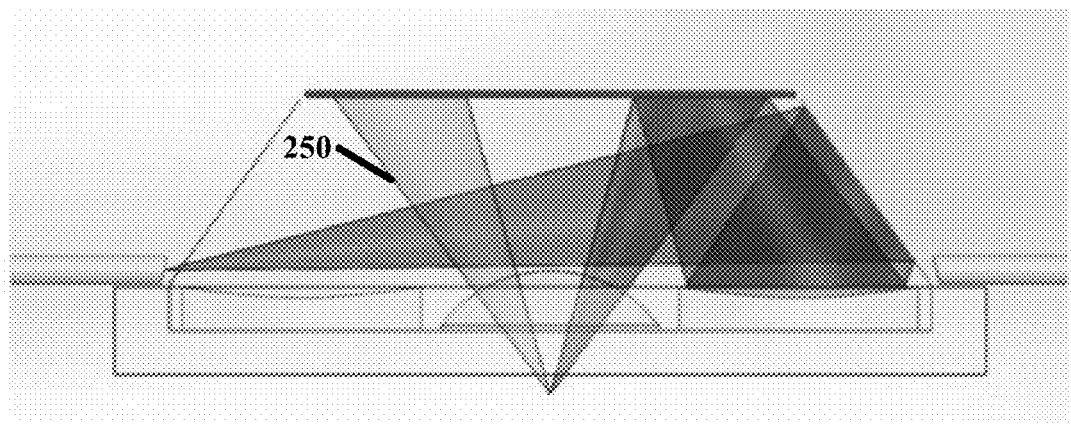
Figure 2F:
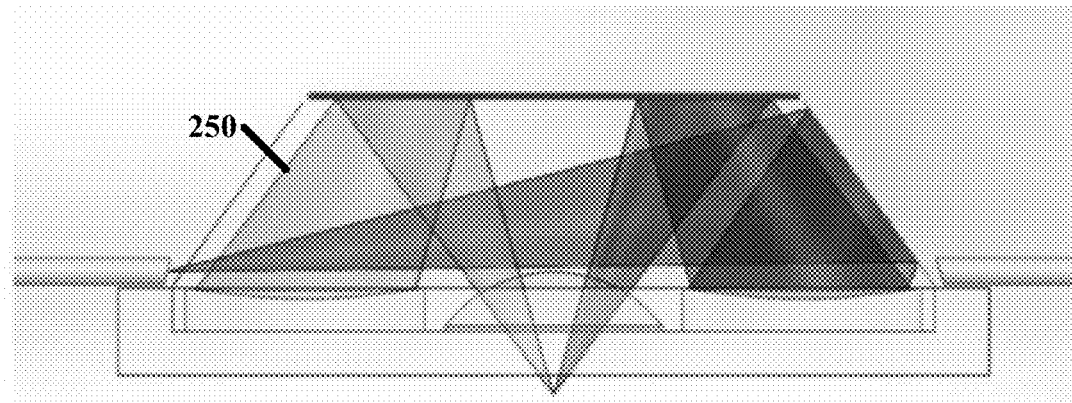
Figure 2G:
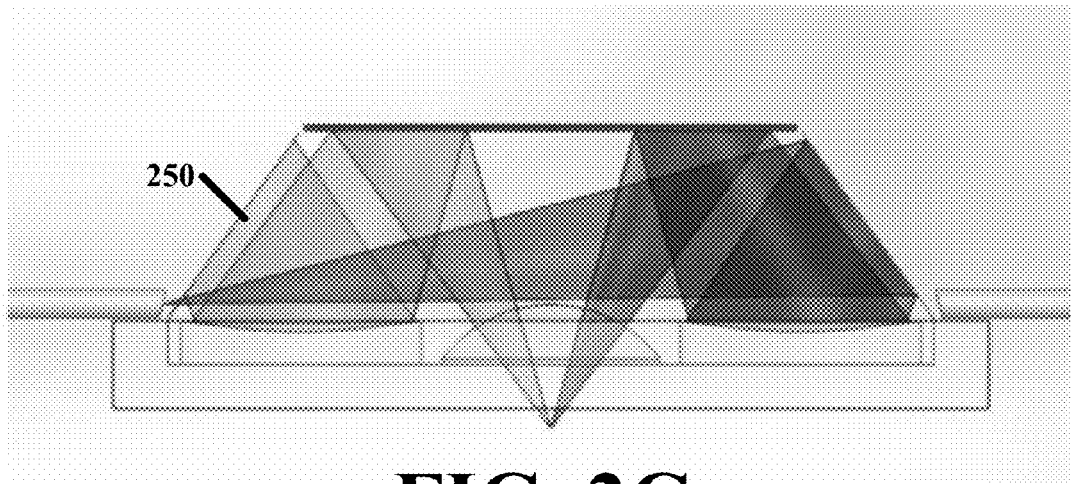
Figure 2H:
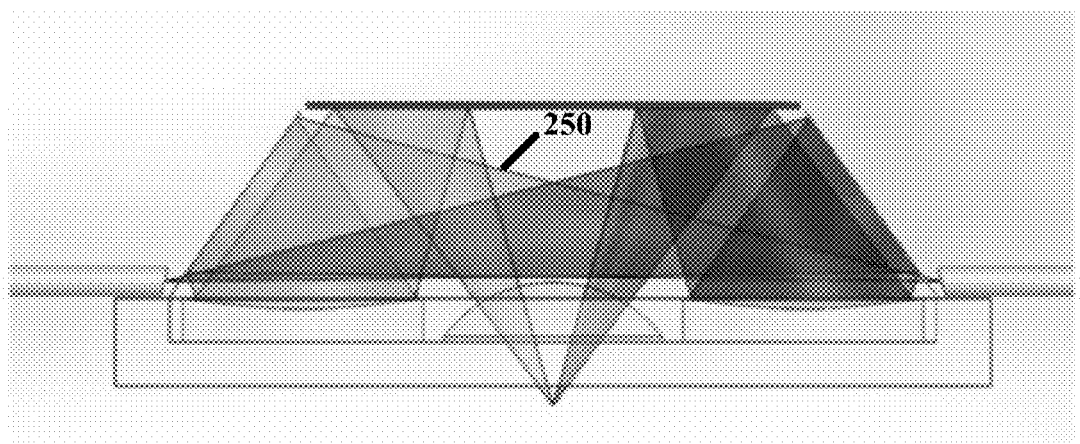

As shown in FIG. 2A, a diverging illumination beam, the light beam 250, is shown emerging from the illumination fiber 240. FIG. 2B shows the light beam 250 deflected from one of the mirrored surfaces 215 inside the spacer region 210. The light beam 250 is directed, via the first of the mirrored surfaces 215, towards one of the curved-shaped mirrors 235, which is integrated into the optics region 225. FIG. 2C shows the light beam 250 focused by the first of the one of the curved-shaped mirrors 235, and the focused light beam 250 is directed to impinge onto the scanning mirror 205. FIG. 2D shows the focused light beam 250 deflected from scanning mirror 205 through the curved-shaped window 230, which is also integrated into the optics region 225. The focused illumination beam is transmitted through the curved-shaped window 230, and into tissue below. FIG. 2E shows the light beam 250 as an expanding signal beam that impinges onto the scanning mirror 205 after passing through the curved-shaped window 230. FIG. 2F shows that the expanding signal beam (the light beam 250) is then deflected off the scanning mirror 205, and directed toward the second of the curved-shaped mirrors 235. FIG. 2G shows the second of the curved-shaped mirrors 235 focusing the light beam 250 and directing the light beam 250 to the second of the mirrored surfaces 215. Finally, FIG. 2H shows the focuses light beam 250 reflected from the second of the mirrored surfaces 215 and directed into the collection fiber 245.

Figure 3:
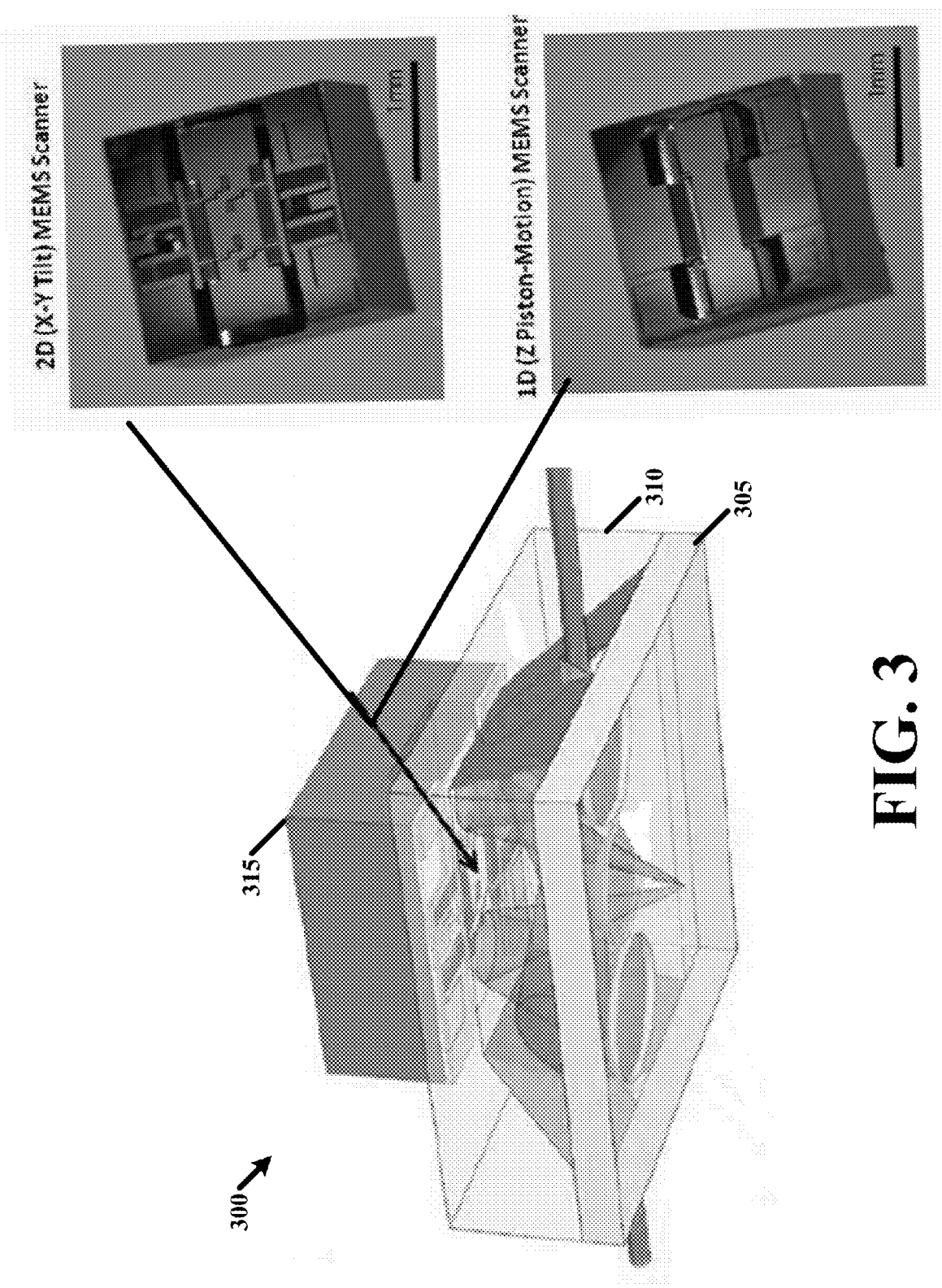
FIG. 3 shows another view of an example sandwiched arrangement, consistent with various aspects of the present disclosure.
Figure 8B:
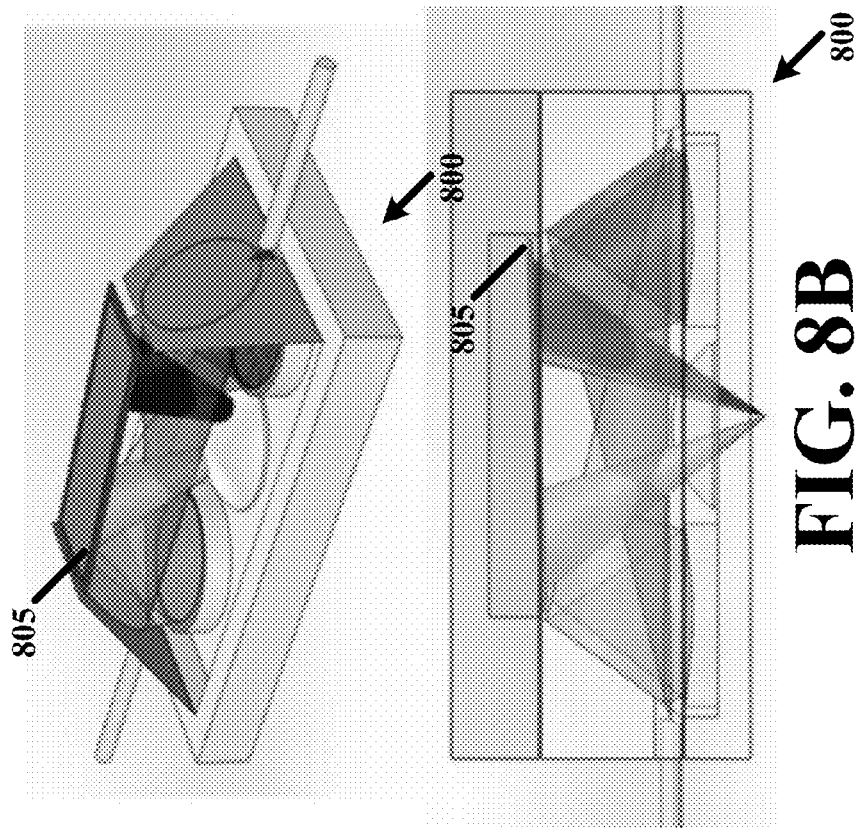
FIGS. 8A-8D show an example operation of a sandwiched arrangement, consistent with various aspects of the present disclosure.
Figure 8A:
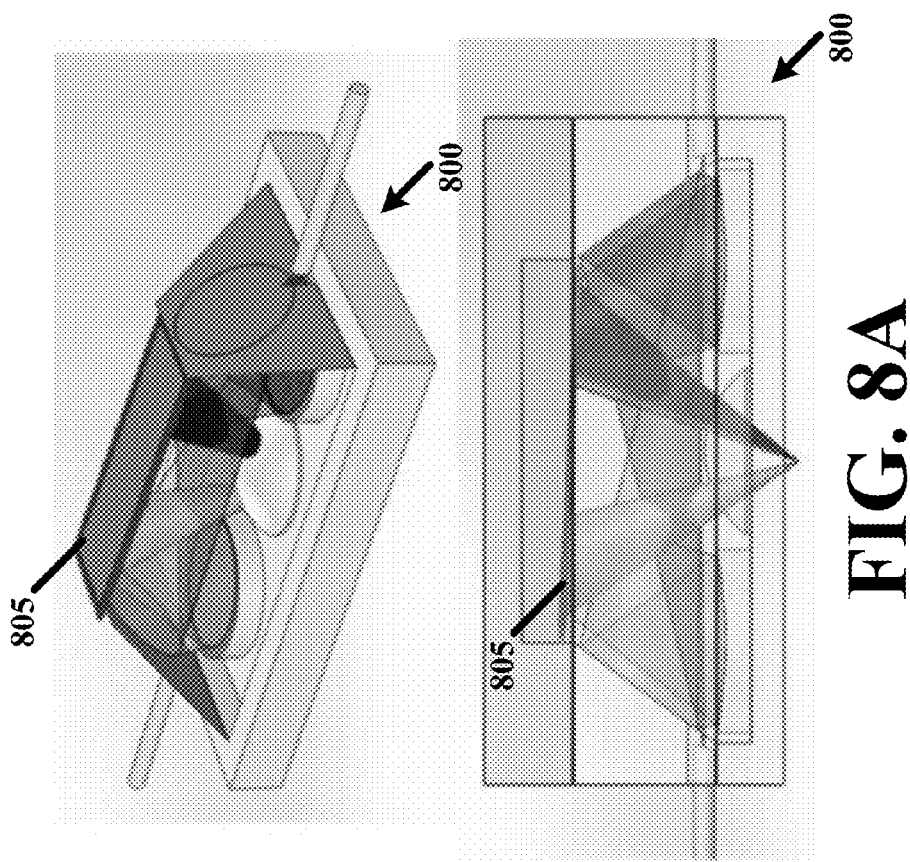
Figure 8D:
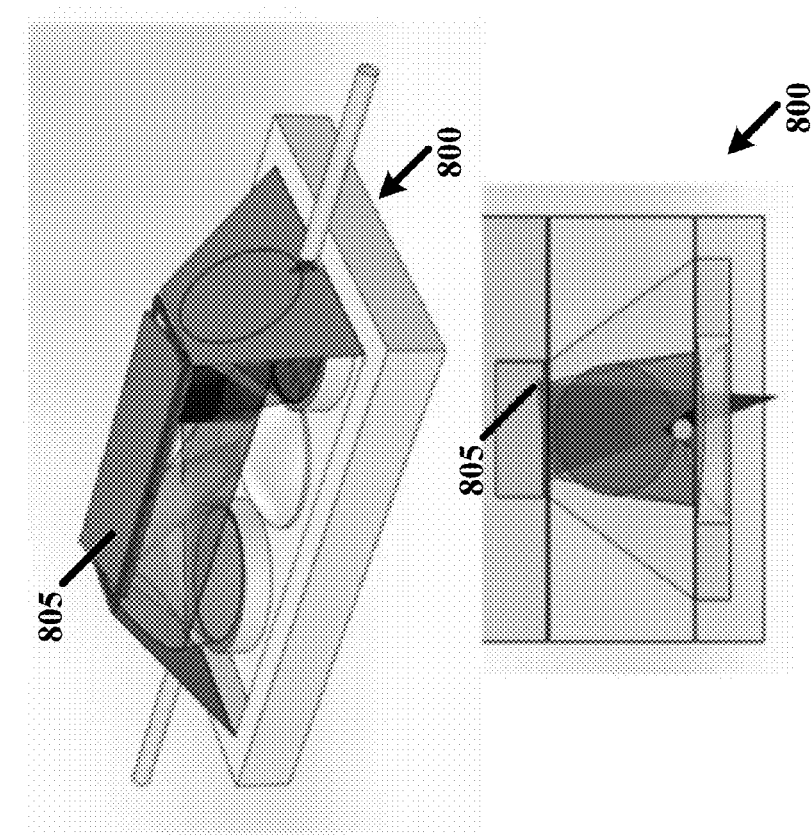
Figure 8C:
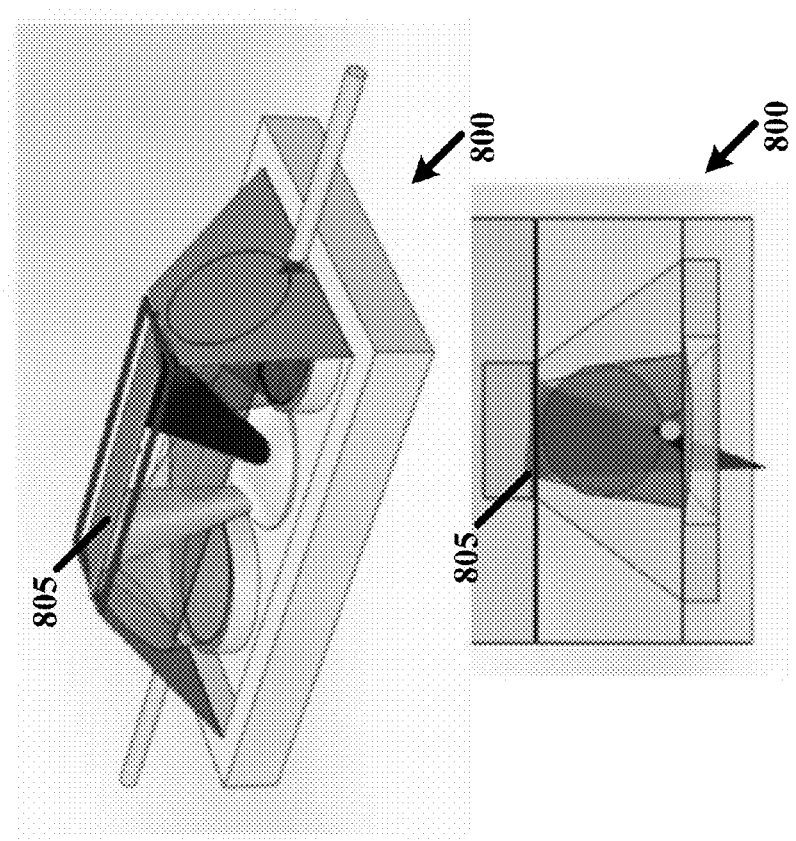

FIG. 3 shows another view of an example sandwiched arrangement 300, consistent with various aspects of the present disclosure. The sandwiched arrangement 300 forms a single monolithic device that has a three-layer stacked structure, which provides an optics layer 305, a spacer 310, and a Microelectromechanical systems (MEMS) scanner layer 315. The MEMS scanner layer 315 provides fast depth scanning of the beams (e.g., within a tissue) by using a high frequency Z-piston-motion mirror that rapidly produces different imaging depths, as is discussed and shown in further detail with reference to FIGS. 8A and 8B. Additionally, the MEMS scanner layer 315 includes a second MEMS scanner, which is placed at 45 degrees with respect to the package axis in order to provide side-looking beams, uses a rapidly oscillating mirror that tilts about the X and Y axes to produce high-frequency scanning of the focused beams, as is discussed and shown in further detail with reference to FIGS. 8C and 8D. This scanning produces an X-Y image plane at any one of the specific image depths determined by the Z-scanner. The first and second MEMS scanners are shown inset in FIG. 3. The scanners are combined in the 3-D MEMS scanner layer 315 as an assembly that provides a high-speed 3-D scanning system, which produces fast 3-D confocal imaging in tissue.

Figure 4:
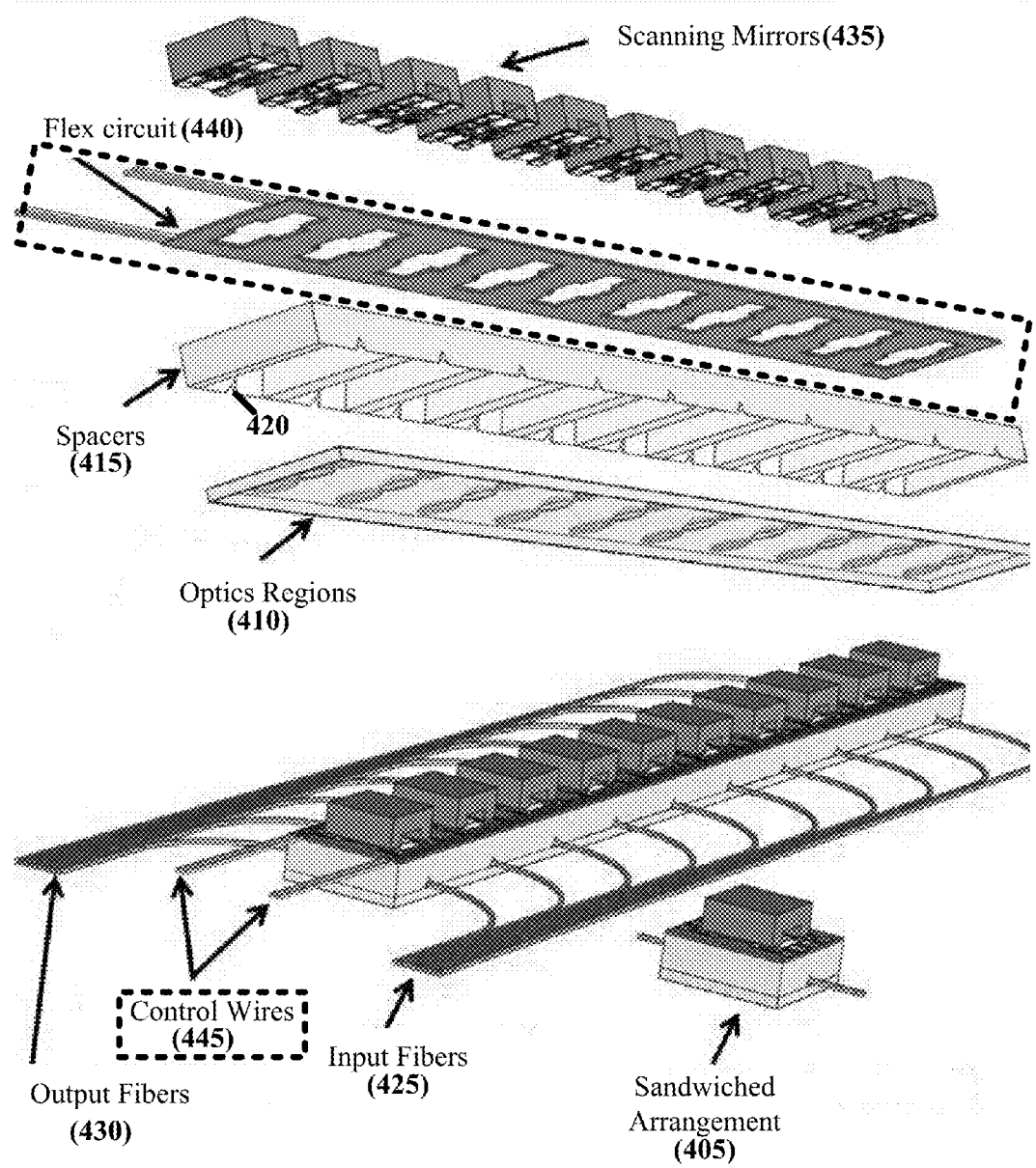
FIG. 4 shows an example array of microscopes that each includes a sandwiched arrangement, consistent with various aspects of the present disclosure.

FIG. 4 shows an example array of microscopes 400 that each includes a sandwiched arrangement 405, consistent with various aspects of the present disclosure. Three primary layers are stacked together to build such an arrayed DAC device/system. The first layer 410 is an integrated optics layer that has a replicated pattern of optical components fabricated within a planer substrate, which is made of an optical material (e.g., fused silica, moldable glass, plastic). The replicated pattern of optics includes curved-shaped mirrors (e.g., elliptical concave mirrors), and a center window, consistent with various aspects of the present disclosure. In certain embodiments, portions of the surfaces in this layer may be coated differently to enhance optical reflection or transmission properties in different regions as needed.

The second layer 415 is a silicon spacer that is stacked atop the first layer and which includes a replicated pattern of cavities, respective to the pattern in the first layer 410, which are etched through the spacer in such a way that the cavity walls act as inclined mirror surfaces, consistent with various aspects of the present disclosure. As described in detail above with reference to, for example, FIG. 1, 2, or 3, the inclined mirror surfaces fold respective illumination and collection beams of light for each microscope. The result is a 3-D configuration of overlapping beams. Other mechanical features may be etched into the second layer 415 such as v-grooves 420 for supporting input 425 and output optical fibers 430. The input 425 and output optical fibers 430, respectively, provide the illumination beams and collect the collection beams for each microscope. Similar to the first layer 410, portions of the surfaces in the second layer 415 may be coated differently to enhance optical reflection properties in different regions as needed.

The third layer 435 is stacked atop the second layer 415. The third layer 435 includes a substrate that has multiple silicon wafers bonded together and micromachined to produce a replicated pattern of MEMS scanners (e.g., as described with reference to FIG. 3). The replicated pattern of MEMS scanners corresponds to the patterns in the first layer 410 and the second layer 415, and is used to synchronously scan the illumination and collection beams (as needed) for operation of each microscope. Similar to the first layer 410 and the second layer 415, portions of the surfaces in the third layer 435 may be coated differently to enhance optical reflection in different regions as needed.

Figure 5:
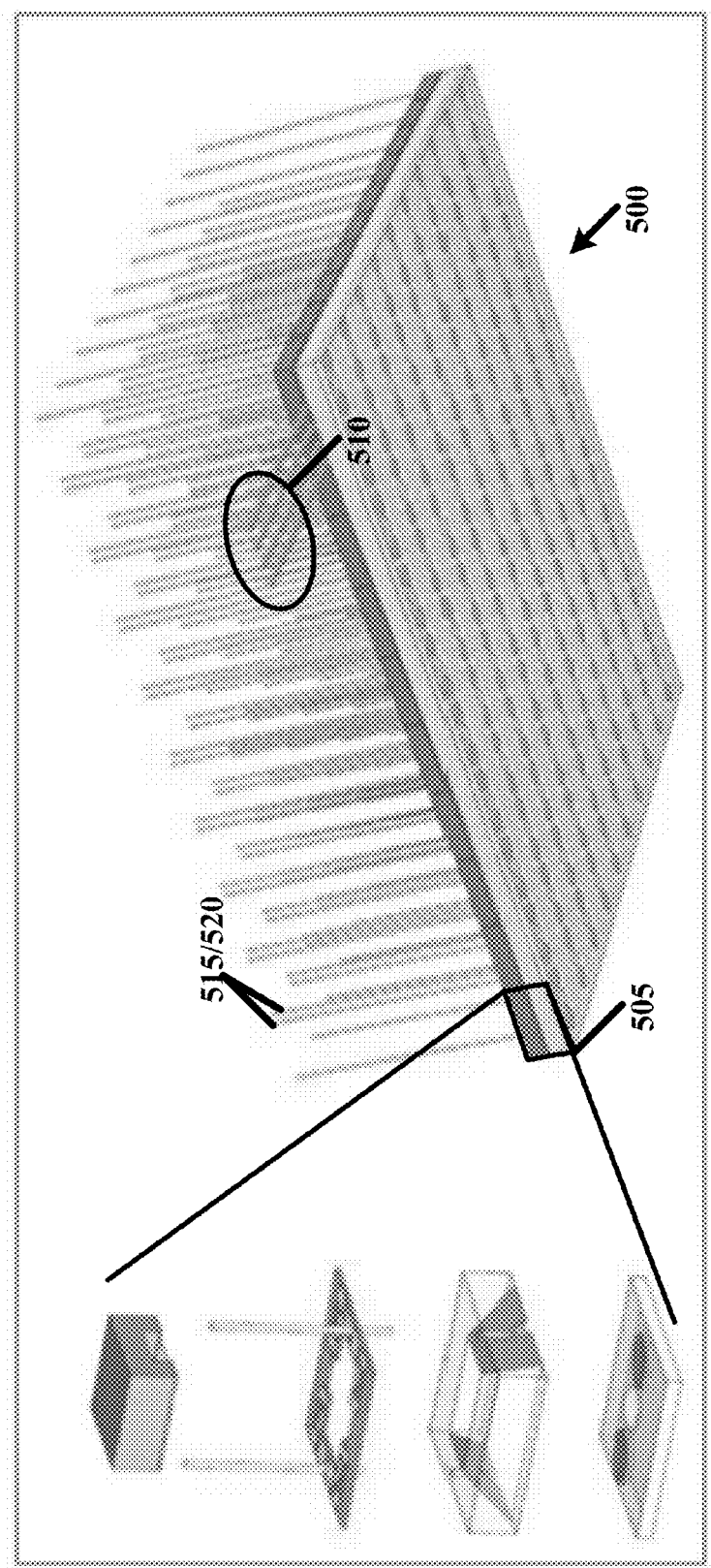
FIG. 5 shows another example array of microscopes that each includes a sandwiched arrangement, consistent with various aspects of the present disclosure.

Optionally, the array of microscopes 400 can be fixed with flex-circuit layer 440 that provides parallel connections for a row of microscopes. In certain arrays of microscopes having greater than one row, for example as shown in FIG. 5, the flex-circuit layer 440 provides parallel connections for each of the multiple rows of microscopes. In such an embodiment, control wires 445 drive each individual row of microscopes. The flex-circuit 440 can also be configured such that separate sets of signal wires are carried to each microscope instead of the parallel configuration.

FIG. 5 shows another example array of microscopes 500 that each includes a sandwiched arrangement 505, consistent with various aspects of the present disclosure. A 100-microscope 2-D array is shown constructed by replicating 10 rows by 10 columns of the sandwiched arrangement 505 in each layer. The electrical connections may be configured to allow all 100 scanners to be driven synchronously by the same driving voltages through control wires 510, such as through the four wires shown. As shown in FIG. 5, input and output fibers 515/520 are placed vertically, and provided to each sandwiched arrangement 505.

In a specific example, the microscope array can have a center-to-center, between each sandwiched arrangement, of 3 by 3 mm. Assuming each sandwiched arrangement has an field-of-view of approximately 300 µm, sequentially stepping through each sandwiched arrangement then in order to image the full area under the array can be achieved through a computer-controlled stage through at least 10 positions along the x-axis and similarly through ten positions along the y-axis for each x-position. This results in each microscope being required to gather 100 separate images during the collection process. The total acquisition time for collecting a complete high-resolution image of tissue that is the same size as the 30 by 30-mm microscope array can depend on the frame rates of the microscopes and the duty cycle of all the microscopes that are each gathering images from their respective locations. At a 100% duty cycle and at 10 frames per second imaging speed of each microscope in the array, for example, the complete high-resolution 3 by 3-cm image can be collected in ten seconds.

In certain embodiments, individual lasers are operated simultaneously (e.g., at a power of approximately 10 mW), or instead, a single higher power laser can be used that has means for providing 100 separate beams (e.g., at a power of approximately 1 W) split off from the main beam and injected into the input fibers. The output fibers can carry the signals to a remotely located bank of detectors. Image stitching software can be used to provide the complete image of the tissue sample.

Figure 6:
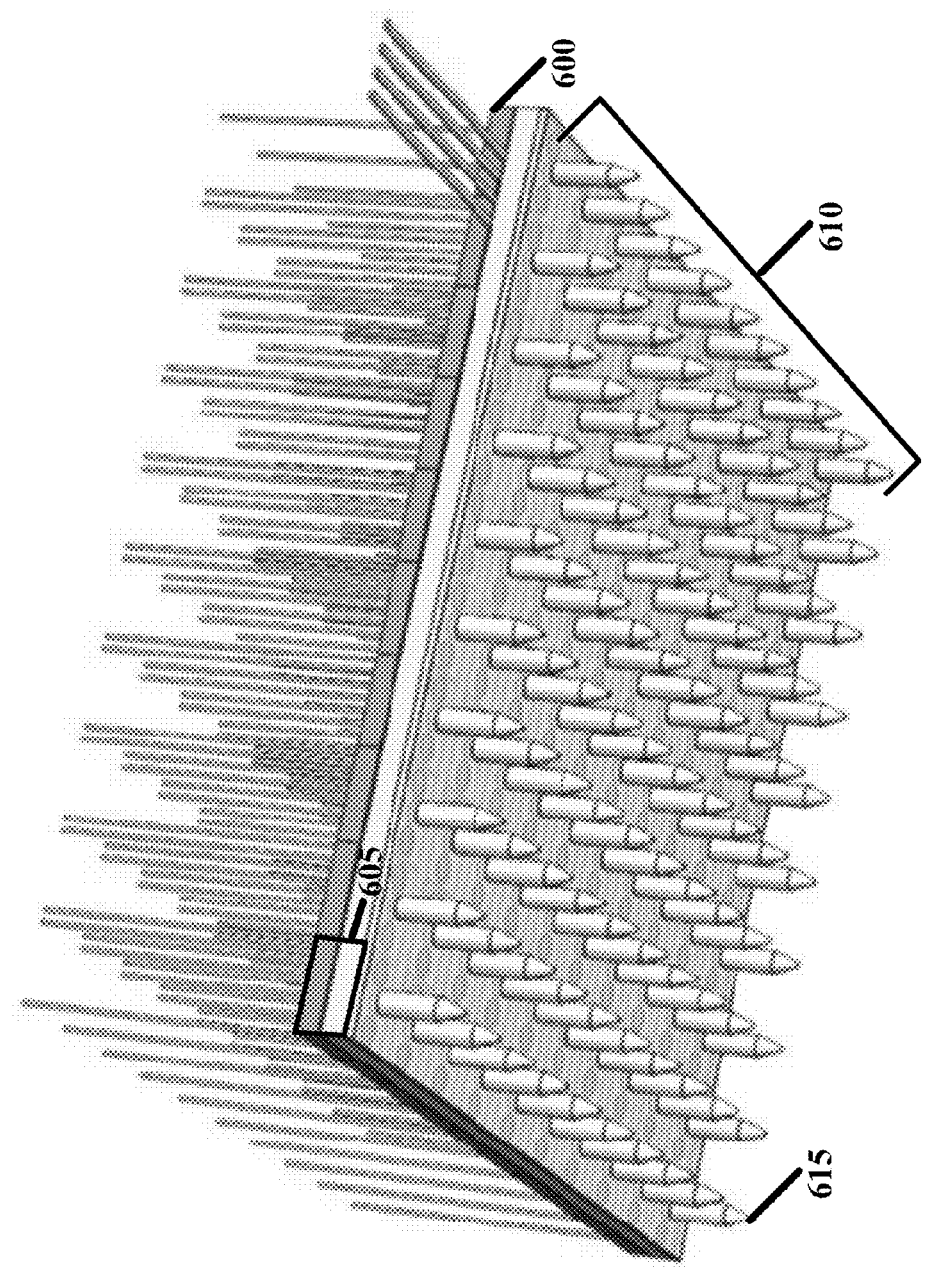
FIG. 6 shows yet another example array of microscopes that each includes a sandwiched arrangement, consistent with various aspects of the present disclosure.

FIG. 6 shows yet another example array of microscopes 600 that each includes a sandwiched arrangement 605, consistent with various aspects of the present disclosure. As shown in FIG. 6, an array of lenses 610 is added as an additional layer. The array of lenses 610 in the embodiment shown is an array of gradient index (GRIN) that provide extended reach into tissues where the biology of interest is below the surface. The lenses can have tapered ends 615 to penetrate the tissue and reach sites of interest.

The additional array of lenses can be useful in allergy testing where each needle lens in an array would be laced with a unique allergen and a dye (e.g., as indocyanin green), and the array of microscopes would be used to image inflammatory cells as they migrate toward the allergen. This would constitute a rapid allergy test that would provide more information as opposed to a test based on redness (or the absence of redness). Additionally, using an array of lenses and an array of microscopes allows for readout in terms of numbers and types of immune cells. Since not all immune activation is an indication of a pathologic allergic response (e.g., redness), this information could better discern which allergens are problematic. Further, an array of lenses and an array of microscopes can be used for transdermal delivery of a variety of therapies and vaccines. Imaging micro-needle arrays would provide an intelligent readout for many of these dermatological applications.

Figure 7:
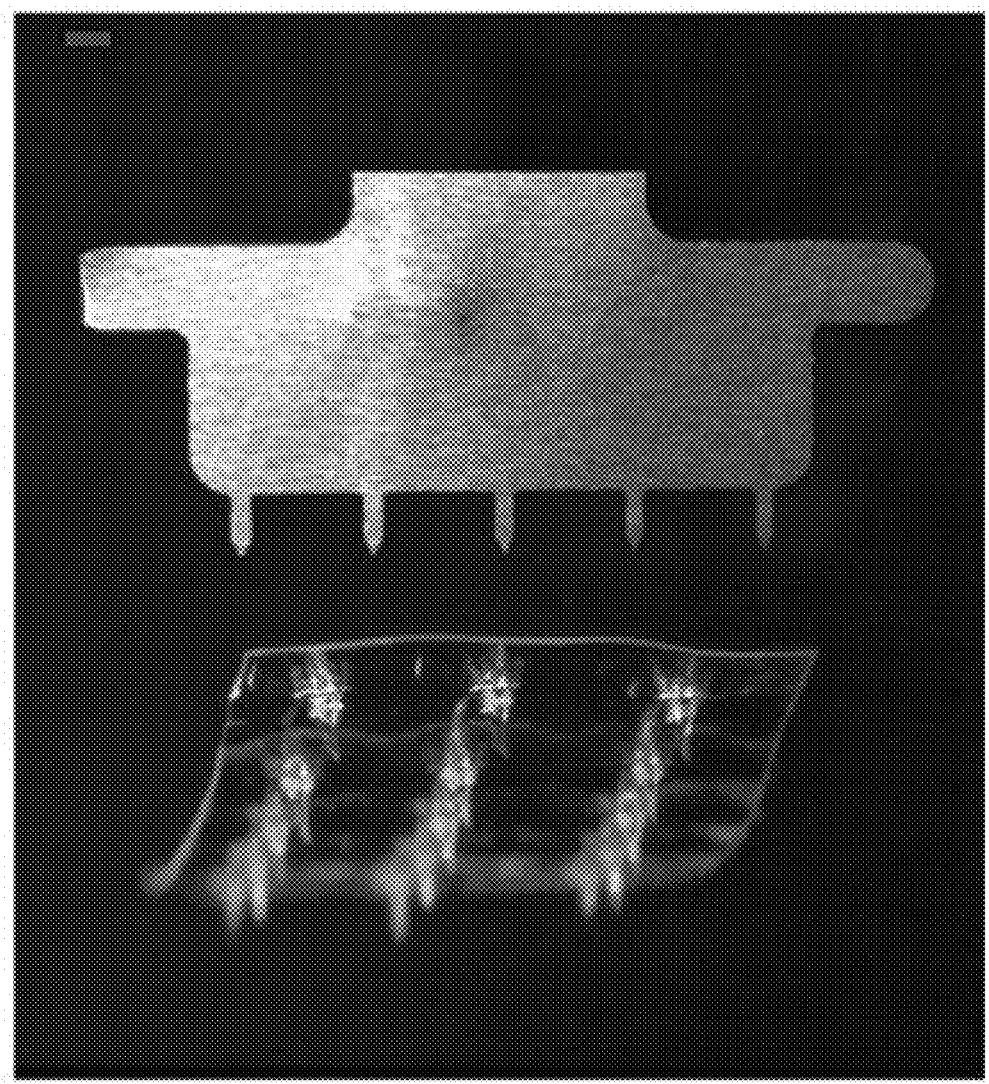
FIG. 7 shows an example needle array, consistent with various aspects of the present disclosure.

FIG. 7 shows an example needle array 700, consistent with various aspects of the present disclosure. As noted above, such needle arrays can penetrate into skin to deliver reagents, and additionally, the tapered GRIN lens can be used in place of a hemispherical interface lens in each sandwiched arrangement to form arrays with needle-lenses.

FIG. 8 shows an example operation of a sandwiched arrangement 800, consistent with various aspects of the present disclosure. As shown in FIGS. 8A/8B, the sandwiched arrangement 800 includes a scanning mirror 805 that can oscillate and alter light beam placement (and the reflection thereof) along a Z image plane within a tissue. Similarly and as shown in FIGS. 8C/8D, the scanning mirror 805 can also oscillate and alter light beam placement (and the reflection thereof) along an X-Y image plane within a tissue.

Figures 9A, 9B:
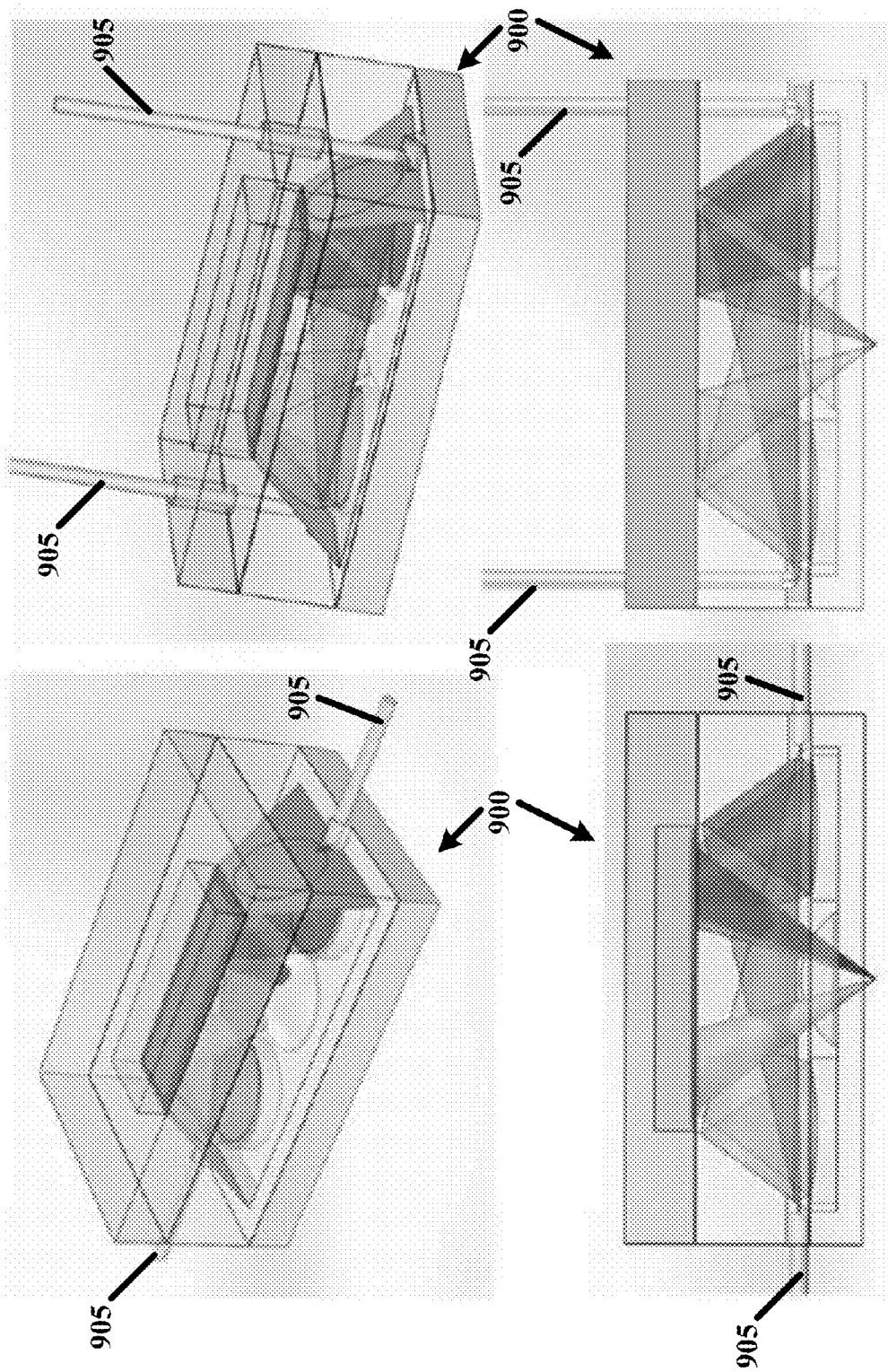
FIGS. 9A and 9B show example arrangements of a sandwiched arrangement including illumination and collection pathways, consistent with various aspects of the present disclosure.

FIGS. 9A and 9B show an example arrangement of a sandwiched arrangement 900 including illumination and collection pathways, consistent with various aspects of the present disclosure. In FIG. 9A, the illumination and collection pathways 905 are provided horizontally relative to the sandwiched arrangement 900, whereas in FIG. 9B, the illumination and collection pathways 905 are provided vertically relative to the sandwiched arrangement 900

Figure 10:
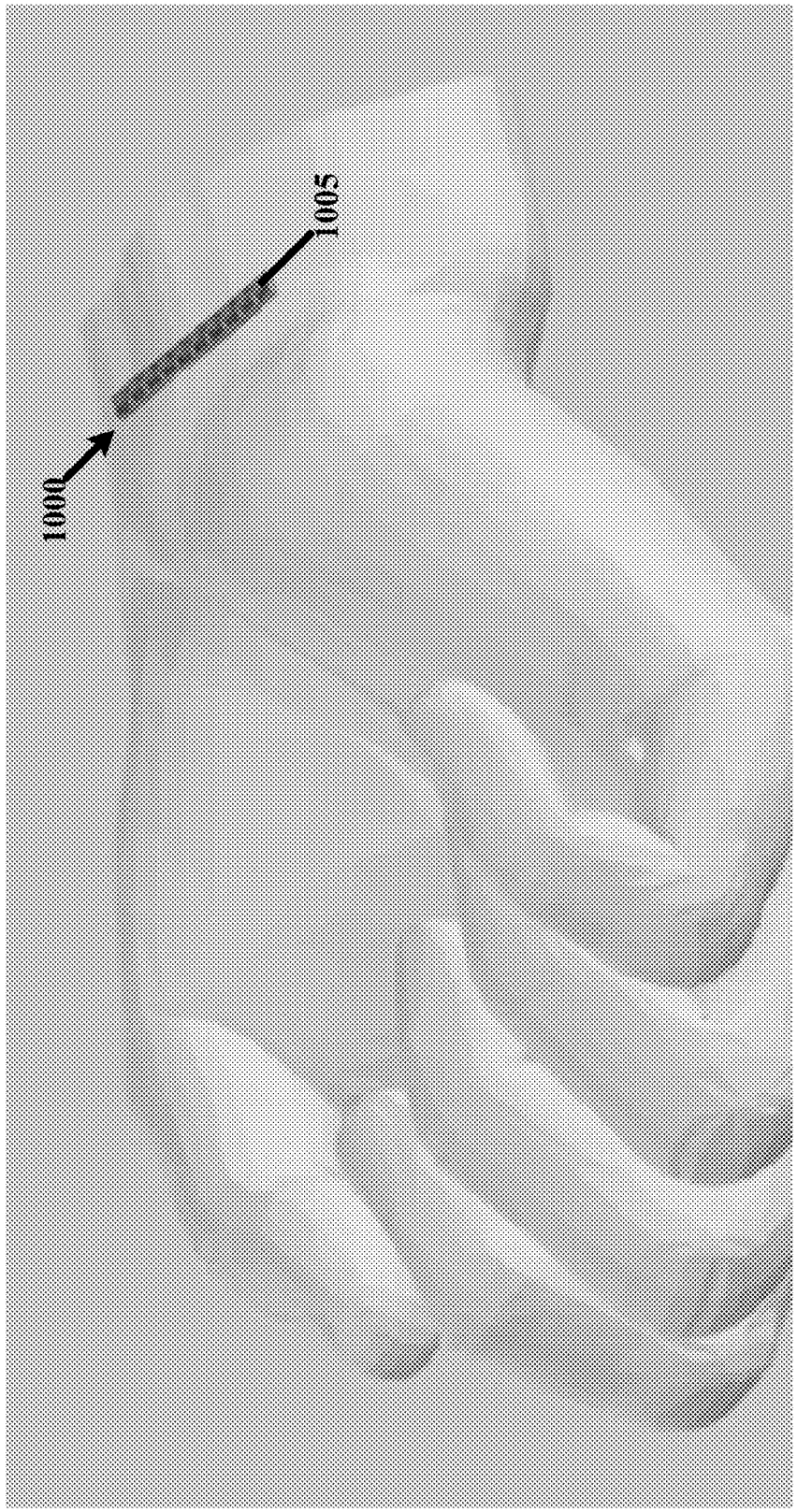
FIG. 10 shows another example array of microscopes that each includes a sandwiched arrangement attached to a patient, consistent with various aspects of the present disclosure.

FIG. 10 shows another example array of microscopes 1000 that each includes a sandwiched arrangement 1005 attached to a patient, consistent with various aspects of the present disclosure. This conceptual drawing shows an in vivo medical diagnostic application using a linear 1×10 array of sandwiched arrangements 1005 forming ten DAC microscopes. The array 1000 can include more than one row, and more sandwiched arrangements 100 per row (e.g., as shown above in FIG. 5). The array 1000 is shown attached to skin for purpose of observing/tracking/counting travelling fluorescently tagged cells in the circulatory system. For example, the tagged cells may be circulating tumor cells that are being monitored during a particular therapeutic intervention as an indication of metastatic potential or disruption of the tumor bed. This configuration could be used for detecting and counting any number of rare cell types including mobilized stem cells, circulating stem cells, immune cells, tumoricidal natural killer cells and others. The array 1000 could be extended into a bracelet style and worn continuously to interrogate the entire blood pool looking for rare cells or for mobilization/activation of cells in immune responses and vaccination strategies.

Various aspects of the present disclosure are directed toward using one or more sandwiched arrangements for assessing cellular status via fluorescence intensity in complex tissue environments including human tissues. In this manner, the sandwiched arrangements can form DAC microscopes, which increases imaging contrast, as compared to previous bench top microscopes, and can image at deeper levels in thick tissue specimens due to a reduction in the multiply-scattered background.

Additionally, aspects of the present disclosure are directed toward using one or more sandwiched arrangements as a DAC microscope that individually is a 3 mm by 3 mm device having a field-of-view of approximately 300-µm. The miniature DAC microscopes, consistent with various aspects of the present disclosure, can be assembled using active alignment techniques. The simplicity and symmetry of the sandwiched arrangements aids in alignment and allows for lower-tolerance assembly of the micro-components. In certain specific embodiments, the sandwiched arrangements provide subcellular resolution (1-5 µm) within a FOV of 300 µm by 300 µm. Moreover, the sandwiched arrangements can provide for imaging one voxel at a time. In certain embodiments, the sandwiched arrangements include low numerical aperture (NA) lenses that have a long working distance.

Various aspects of the present disclosure are also directed toward use of the sandwiched arrangements to detect cancer cells at the margins of resected tissue. The sandwiched arrangements can allow for maximizing of resolution, increasing of the field of coverage, and increasing scan rates to allow large surface areas of samples to be examined quickly (as compared to bench top microscopes). Examining (micro)anatomic changes in tissue architecture and cell features that are characteristic of malignancies is enhanced by the use of miniaturization devices, such as the sandwiched arrangements of the present disclosure formed as high density microscope arrays. The high density microscope arrays can provide a combined FOV that is two-orders of magnitude larger, thus increasing the effective imaging speed by 100× for obtaining high resolution images covering large areas, as compared to a bench top microscope or single microscope. The arrays can be used at the cutting bench in the surgical pathology suite to increase the amount of tissue analyzed in gross pathology, link macroscopic inspection of tissue to microscopic examination and provide more information, more rapidly, than previous approaches.

For guided pathology, evaluating tumor margins and advancing molecular pathology benefits from the use of arrays of microscopes, consistent with various aspects of the present disclosure, that have a combined FOV to permit observation of microanatomic features of thick tissues with rapid wide area coverage such that margins can be completely assessed. The DAC microscopes are versatile, multispectral, and small enough for endoscopic clinical use. To effectively study tumor margins in surgically excised cancer tissues and improve patient care by refining tissue assessment, miniaturization of microscopes and integrating the microscopes into arrays increases the amount of tissue analyzed and used in human patients for early cancer detection, is being applied to image-guided resection to allow for high throughput of images by multiplying the number of imaging units within a single device.

Various aspects of the present disclosure are directed toward lithographic fabrication techniques of manufacturing micro-opto-electro-mechanical systems (MOEMS). The scan mirrors, as described in detail above, can be made as arrays, and the individual mirrors can be diced for assembly into handheld and implantable microscopes. The MEMS components can be created as layers in arrays that are assembled as a sandwiched structure of confocal microscopes. The confocal design illuminates on one axis and collects light on another axis, hence confocal architecture being a dual-axis confocal (DAC) microscope. Thus, rather than physically sectioning, staining and examining small amounts of resected tissue for pathological analysis, freshly excised bulk tissue can be stained and examined. This reduces the time and distance between the diagnostic event and the patient and improves patient care by advancing point-of-care pathology. The arrays can be used to analyze resected cancer tissues and monitor circulating tumor cells (CTC's), in certain embodiments. As a specific example of use, local recurrences in breast cancer are thought to be largely due to undetected residual tumors at the margins. An array of microscopes, consistent with various aspects of the present disclosure, allows for comprehensive en face examination of an entire lumpectomy specimen at cellular resolution and molecular specificity through the microscopes spanning the margins. This sort of examination could be valuable for many other specimens as well. Further, the sandwiched arrangements, individually and as arrays, can be used in the selection of tissue for processing at a surgical pathology bench by providing instant feedback and prospective quality control for specimens submitted for microscopic evaluation. Further yet, images captured by the sandwiched arrangements can be reproduced as Hematoxylin and Eosin (H&E images).

The pathology work flow primarily consists of dissection of the gross specimen, and imaging in the gross room, followed by sign-out of the images, with tissue sampling only for molecular evaluation. Aspects of the present disclosure can eliminate the histology lab from evaluation of most specimens thus saving the healthcare system significant costs and increase the speed at which pathology could be reported. Minimal processing times through the histology lab, including fixation, processing, cutting and staining are about 6-8 hours, with the standard being 24 hours, which would be vastly decreased by the DAC microscopes.

The microscopic appearance of tumor margins determines the likelihood of local recurrence after resection and may be predictive of metastatic potential. Evaluating the entire surface area at an acceptable resolution can reveal the physical properties of a cell. To evaluate large surface areas of resected tumor tissue with microscopic resolution can require a paradigm shift in gross pathology. The sandwiched arrangements address this unmet need when used as arrays of confocal microscopes that can rapidly interrogate the physical properties of tumor cells and their microenvironment over large areas of thick, freshly excised tissues. This can guide a pathologist and aid in diagnosis and prognosis. For instance, embodiments of the present disclosure are directed toward an arrayed dual axis confocal (ADAC) system approximately the size of a small tablet computer with a 3 cm by 3 cm window on top for placing tissue specimens. Such a system can provide cellular-level images of tissue architecture and molecular signatures at 1-3 µm resolution, and can be applied to the pathologic assessment of tumor margins.

For further details regarding confocal microscopy and the sandwiched arrangements (including arrays thereof), consistent with various aspects of the present disclosure, reference is made to U.S. Provisional Patent Application Ser. No. 61/782,384 filed on Mar. 14, 2013, to which priority is claimed, and entitled "Arrayed Dual Axis Confocal Microscopes;" this patent document and its accompanying Appendix A are fully incorporated herein by reference.

Based upon the above discussion and illustrations, those skilled in the art will readily recognize that various modifications and changes may be made to the various embodiments without strictly following the exemplary embodiments and applications illustrated and described herein. For example, one skilled in the art would recognize that certain aspects, such as the curved-window or curved-mirrors, can be different shapes, sizes, and/or arrangements without departing from the true spirit and scope of various aspects of the invention. Further, the various embodiments described herein may be combined in certain embodiments, and various aspects of individual embodiments may be implemented as separate embodiments. Such modifications do not depart from the true spirit and scope of various aspects of the invention, including aspects set forth in the claims.

The invention claimed is:

1. An apparatus comprising:
   a sandwiched arrangement of a plurality of confocal microscopes that form an array, the arrangement including
      a plurality of light-access ports,
      a plurality of scanning mirrors,
      a substrate with a pattern of optical components being replicated as part of the substrate to form an array of curved-shaped mirrors and windows, and
      a spacer including a pattern of replicated cavities in the spacer, the replicated cavities configured and arranged to direct light between the plurality of light-access ports and the array of curved-shaped mirrors using inclined mirrored surfaces in the cavities, and to separate the scanning mirrors and the substrate;
   wherein each confocal microscope in the plurality of confocal microscopes is configured and arranged to:
      provide a field of view by communicating beams of light between a corresponding target region, located in a direction opposite a corresponding scanning mirror, and a corresponding light-directing optical region; and
      fold light beams, as conveyed between a corresponding light-access port and a corresponding curved-shaped window, by reflecting the light beams off a corresponding scanning mirror, the corresponding curved-shaped mirror and a corresponding inclined mirrored surface.

2. The apparatus of claim 1, wherein the windows are hemispherical windows, and the curved-shaped mirrors are ellipsoidal mirrors, and wherein the inclined mirrored surfaces in the spacer are oppositely situated near end regions of a replicated first pattern of the optics region.

3. The apparatus of claim 1, further comprising a scanning mirror substrate that is bonded with the plurality of scanning mirrors.

4. The apparatus of claim 1, further including a flex circuit configured to provide connections to the confocal microscopes, each connection configured to control movement of a corresponding scanning mirror of the plurality of scanning mirrors.

5. The apparatus of claim 1, wherein the plurality of confocal microscopes are arranged in a single row forming a linear array and the spacer includes grooves for receiving a plurality of optical fibers that are connected to the plurality of light-access ports.

6. The apparatus of claim 1, wherein the plurality of confocal microscopes are arranged in an X-by-Y array of confocal microscopes, wherein each of X and Y is two or greater.

7. The apparatus of claim 1, wherein the sandwiched arrangement includes flex circuitry including connections to the plurality of scanning mirrors, the flex circuitry configured and arranged to control movement of the scanning mirrors during the capture of images.

8. The apparatus of claim 1, wherein a surface of the substrate is configured and arranged to interface with a tissue region, and the sandwiched arrangement includes a plurality of optical fiber pairs, each optical fiber pair connected to the light-access ports of a respective confocal microscope of the plurality of confocal microscopes.

9. The apparatus of claim 8, wherein each confocal microscope of the plurality of confocal microscopes is configured and arranged to capture images of the tissue region at a resolution between 1-5 µm and a field-of-view of at least 300 µm by 300 µm.

10. The apparatus of claim 9, wherein the plurality of confocal microscopes are arranged in an array, that is at least 10-by-10, the sandwiched arrangement further includes a flex circuit that includes control wires that are configured to synchronously drive each of the scanning mirrors using the same driving voltages at each scanning mirror and the plurality of confocal microscopes are configured to capture a 3 centimeter by 3 centimeter image in 10 seconds.

11. The apparatus of claim 10, wherein the plurality of optical fiber pairs are vertically coupled to the plurality of light-access ports from a side of the substrate opposite the surface of the substrate.

12. The apparatus of claim 1, wherein the windows are tapered gradient-index (GRIN) lenses that each includes a tip configured and arranged to penetrate tissue, and to focus beams of light near the tip.

13. A method for use in a sandwiched arrangement of a plurality of confocal microscopes that form an array, the arrangement including a plurality of light-access ports, a plurality of scanning mirrors, and a substrate with a pattern of optical components being replicated as part of the substrate to form an array of curve-shaped mirrors and windows, the method comprising:
   using a spacer, that includes a pattern of replicated cavities in the spacer, to separate the scanning mirrors and the substrate;
   reflecting, using the plurality of curved-shaped mirrors, light between the light-access ports and the windows; and
      for each confocal microscope and corresponding components, folding beams of light between a light access port of the light access ports and a target region by:
         using a window of the windows to provide a field of view by communicating beams of light between a scanning mirror of the scanning mirrors and the target region, located in a direction opposite the scanning mirror; and
         using a curved-shaped mirror of the curved-shaped mirrors to reflect light between the scanning mirror and a mirrored surface of the mirrored surfaces.

14. The method of claim 13, further including using the plurality of confocal microscopes to inspect a target area via respective fields of view provided by the plurality of confocal microscopes.

15. The method of claim 14, further comprising driving scanning mirrors for individual rows of the confocal microscopes using parallel connections within each of the individual rows.

16. The method of claim 13, wherein the windows are gradient index (GRIN) lenses.

17. The method of claim 16, wherein the GRIN lenses are tapered and further comprising placing different allergens on the GRIN lenses, puncturing tissue with the tapered GRIN lenses and detecting inflammatory cells from images captured by the plurality of confocal microscopes.

* * * * *